(12) United States Patent
Tung et al.

(10) Patent No.: US 7,214,839 B2
(45) Date of Patent: May 8, 2007

(54) METHOD OF MAKING HYDROFLUOROCARBONS

(75) Inventors: Hsueh Sung Tung, Getzville, NY (US); Chad L. Marks, Gonzales, LA (US); Stephen A. Cottrell, Baton Rouge, LA (US)

(73) Assignee: Honeywell International Inc., Morristown, NJ (US)

( * ) Notice: Subject to any disclaimer, the term of this patent is extended or adjusted under 35 U.S.C. 154(b) by 127 days.

(21) Appl. No.: 10/444,610

(22) Filed: May 23, 2003

(65) Prior Publication Data

US 2004/0236160 A1 Nov. 25, 2004

(51) Int. Cl.
*C07C 17/00* (2006.01)

(52) U.S. Cl. .................. 570/163; 570/164; 570/166; 570/167; 570/168; 570/169; 570/170

(58) Field of Classification Search ............. 570/163, 570/164, 166, 167, 168, 169, 170
See application file for complete search history.

(56) References Cited

U.S. PATENT DOCUMENTS

| | | | |
|---|---|---|---|
| 2,942,036 A | 6/1960 | Smith et al. ............. 260/653 |
| 5,171,901 A | 12/1992 | Gassen et al. ............. 570/168 |
| 5,574,192 A | 11/1996 | VanDerPuy et al. ........ 570/167 |
| 5,710,352 A * | 1/1998 | Tung ........................... 570/166 |
| 5,744,660 A | 4/1998 | Bradley et al. ............. 570/169 |
| 5,763,706 A | 6/1998 | Tung et al. .................. 570/167 |
| 5,763,708 A | 6/1998 | Clemmer et al. ........... 570/169 |
| 5,770,779 A * | 6/1998 | Nappa et al. ............... 570/166 |
| 5,877,359 A | 3/1999 | Elsheikh ..................... 570/160 |
| 5,902,912 A * | 5/1999 | Tung et al. .................. 570/164 |
| 6,187,976 B1 | 2/2001 | Van Der Puy et al. ..... 570/176 |
| 6,362,383 B1 * | 3/2002 | Wilmet et al. .............. 570/166 |
| 6,479,718 B1 | 11/2002 | Elsheikh et al. ............ 570/167 |
| 6,730,817 B1 | 5/2004 | Wilmet et al. .............. 570/167 |

* cited by examiner

*Primary Examiner*—Sikarl A. Witherspoon
(74) *Attorney, Agent, or Firm*—Colleen D. Szuch

(57) ABSTRACT

A manufacturing process for making hydrofluorocarbons (HFCs), by reacting a hydrochlorocarbon and HF in a liquid phase catalytic reactor using a large mole ratio of HF to hydrochlorocarbon to minimize formation of high boiling by-products and improve HF consumption and hydrofluorocarbon yields.

30 Claims, No Drawings

METHOD OF MAKING HYDROFLUOROCARBONS

BACKGROUND OF THE INVENTION

The present invention relates to the preparation of hydrofluorocarbons (HFC's). More particularly, the invention pertains to a method for the preparation of difluoromethane (HFC-32), 1,1,1-trifluoroethane (HFC-143a), 1,1,1,3,3-pentafluoropropane (HFC-245fa), 1,1,1,3,3,3-hexfluoropropane (HFC-236fa), 1,1,1,3,3-pentafluorobutane (HFC-365mfc) by reacting the corresponding hydrochlorocarbon feedstocks and HF in a liquid phase catalytic reactor using a large mole ratio of HF to hydrochlorocarbon to minimize formation of high boiling by-products and improve HF consumption and hydrofluorocarbon yields.

In recent years there has been widespread concern that chlorofluorocarbons might be detrimental to the Earth's ozone layer. As a result, there is a worldwide effort to use halocarbons which contain fewer chlorine substituents. In this regard, 1,1,1,3,3-pentafluoropropane and other HFC's have zero ozone depletion potential, and are being considered as a replacement for chlorofluorocarbons in many applications. The production of hydrofluorocarbons, i.e. compounds containing only carbon, hydrogen and fluorine has been the subject of interest to provide environmentally desirable products for use as solvents, foam blowing agents, refrigerants, cleaning agents, aerosol propellants, heat transfer media, dielectrics, fire extinguishing compositions and power cycle working fluids. It is known in the art to produce hydrofluorocarbons by reacting hydrogen fluoride with various hydrochlorocarbon compounds. Such HFC's are not only considered to be much more environmentally advantageous than hydrochlorofluorocarbons (HCFC's) or chlorofluorocarbons (CFC's) because they are non-ozone depleting, but also is they are also non-flammable and non-toxic as compared to the chlorine containing compounds. Hydrofluorocarbons are themselves well known. For example, HFC-245fa itself is well known in the art as described in U.S. Pat. No. 2,942,036, which is incorporated herein by reference. It has been a problem in the art to conduct an economical process for the continuous preparation of hydrofluorocarbons. One such process has been disclosed in U.S. Pat. No. 5,763,706, which is incorporated herein by reference. This reference shows reacting 1,1,1,3,3-pentachloropropane (HCC-240fa) and 1,1,1,3,3,3-hexachloropropane (HCC-230fa) with hydrogen fluoride in the presence of a fluorination catalyst, however, this process employs a relatively low molar ratio of hydrogen fluoride to HCC-240fa or HCC-230fa. This technique produces a disadvantageously large amounts of high boiling point by-products and a lower than desired catalyst life. It has now been found that by the use of a large HF to hydrochlorocarbon (organic feed) ratio, of at least about 15:1 in the liquid phase, the reaction can reduce high boiling point by-product formation and also prolong catalyst life. This is opposed to the prior art teaching to use organic-rich, HF-lean conditions.

It has now been found that hydrofluorocarbons, such as HFC-32, HFC-143a, HFC-245fa, HFC-236fa, HFC-365mfc, but not limited thereto, may be continuously and economically produced in an integrated manufacturing process by the reaction of hydrochlorocarbons with a high mole ratio of hydrogen fluoride. The hydrochlorocarbon and HF are first reacted, in either the liquid or vapor phase, but preferably in a liquid phase catalytic reaction, and a portion of the excess amounts of HF is optionally recycled back to the reactor such as by using a recycle column. HCl is then optionally removed by distillation, additional HF is recovered, such as by liquid-vapor or liquid-liquid extraction and then optionally recycled. Unsaturates are thereafter removed by photochlorination and hydrofluorocarbons are obtained by distillation.

DESCRIPTION OF THE INVENTION

The invention provides a process for the preparation of a hydrofluorocarbon which comprises
  (a) reacting at least one hydrochlorocarbon with hydrogen fluoride in the presence of a fluorination catalyst, wherein the hydrogen fluoride to hydrochlorocarbon mole ratio is at least about 15:1;
  (b) optionally recycling a portion of any unreacted HF back to step (a);
  (c) optionally removing any HCl produced by step (a); and
  (d) recovering at least one hydrofluorocarbon.

The invention also provides a process for the preparation of a hydrofluorocarbon which comprises (a) reacting at least one hydrochlorocarbon with hydrogen fluoride, in the presence of a fluorination catalyst, and wherein the hydrogen fluoride to hydrochlorocarbon mole ratio is at least about 15:1;
  (b) optionally recycling a portion of any unreacted HF back to step (a);
  (c) optionally removing any HCl produced by step (a);
  (d) optionally recovering any additional unreacted HF present after step (c) by liquid-vapor or liquid-liquid extraction;
  (e) optionally removing unsaturated compounds present after step (d) by photochlorination; and
  (f) recovering at least one hydrofluorocarbon from the result of step (e) by distillation.

Useful hydrochlorocarbons for this invention non-exclusively include methylene chloride ($CH_2Cl_2$), for the production of difluoroethane $CH_2F_2$ (HFC-32); 1,1,1-trichloroethane (HCC-140a) for the production of 1,1,1-trifluoroethane (HFC-143a); 1,1,1,3,3-pentachloropropane (HCC-240fa) for the production of 1,1,1,3,3,-pentafluoropropane (HFC-245fa); 1,1,1,3,3,3-hexachloropropane (HCC-230fa) for the production of 1,1,1,3,3,3-hexafluoropropane (HFC-236fa); 1,1,1,3,3-pentachlorobutane (HCC-360jfa) for the production of 1,1,1,3,3-pentafluorobutane (HFC-365mfc) and combinations thereof. 1,1,1,3,3-pentachloropropane (HCC-240fa) can also be used for the production of 1-chloro,3-3-3-trifluoropropene (HCFC-1233zd) and 1,3,3,3-tetrafluoropropene (HFC-1234ze). Perchloroethylene can be used to produce 1,1,1,3,3-pentrafluoroethane (HFC-125).

In the practice of the present invention, a fluorination catalyst, preferably a liquid phase catalyst is charged to a fluorination reactor prior to heating of the reactor. Useful fluorination catalysts non-exclusively include transition metal halides, and oxides, Group IVb metal halides and Group Vb metal halides and mixtures thereof. Such catalysts non-exclusively include fluorinated chrome halides, fluorinated chrome oxides, fluorinated species of $SbCl_5$, $SbCl_3$, $TaCl_5$, $SnCl_4$, $NbCl_5$, $TiCl_4$, or $MoCl_5$ and combinations thereof. The reactor according to this invention may be any suitable fluorination reaction vessel but are preferably constructed from materials which are resistant to the corrosive effects of hydrogen fluoride such as Hastalloy, Inconel, Monel and fluoropolymer-lined vessels. At least one hydrochlorocarbon and HF are simultaneously fed to the reactor after the reactor reaches the desired temperature. An important feature of the invention is that the hydrogen fluoride to hydrochlorocarbon mole ratio ranges from about 15:1 to about 50:1.

In a preferred embodiment, the hydrogen fluoride to hydrochlorocarbon mole ratio ranges from about 15:1 to about 40:1 and in a more preferred embodiment, the hydrogen fluoride to hydrochlorocarbon mole ratio ranges from about 20:1 to about 30:1. The reactor is run at a preferred temperature ranging from about 60° C. to about 180° C.; more preferably from about 70° C. to about 150° C. and most preferably from about 80° C. to about 120° C. Reactor pressure is usually maintained at a pressure of from about 20 to about 400 psig, preferably from about 50 to about 300 psig; more preferably from about 100 to about 275 psig and most preferably from about 125 to about 260 psig. A chlorine feed is optional, but preferred to keep the catalyst active. A chlorine feed is especially advantageous when antimony chloride is used as catalyst. For every pound of catalysts, such as $SbCl_5$ catalyst, about 0.002 to about 0.2 lb per hour of chlorine is fed to the reactor. Chlorine can be charged in either a batch or continuous mode.

Optionally, but preferably, a top catalyst stripper is used such that most of the unreacted HF and catalyst is refluxed back to the reactor. The catalyst stripper is equipped with a distillation column and a condenser and this step is conducted by adjusting the temperature of the condenser to a range of from about 20° C. to about 200° C. The effluent from the catalyst stripper is optionally, but preferably fed to a recycle column to recycle a portion of the excess amounts of HF. The pressure of the recycle column is preferred to match that of the reactor.

The effluent from the recycle column is then optionally, but preferably, fed to an HCl distillation column to remove relatively pure HCl from the reaction mixture exiting the recycle column. The pressure of the HCl column is preferred to match that of the recycle column. In another embodiment, unreacted HF can be recovered at this point in the process and with optional recycling of recovered hydrogen fluoride back to the reactor in step (a).

The essentially HCl free organic/HF mixture exiting the HCl column is optionally fed to HF recovery unit. The mixture of fluorocarbons resulting from step (c) is in admixture with hydrogen fluoride. The hydrofluorocarbon and HF may be separated by extracting the HF/hydrofluorocarbon mixture with sulfuric acid. This forms a phase rich in HFC and a phase rich in the hydrogen fluoride and sulfuric acid. Sulfuric acid is preferably added such that the weight ratio of sulfuric acid to hydrogen fluoride ranges from about 1:1 to about 25:1. More preferably the weight ratio ranges from about 1:1 to about 20:1 and most preferably from about 2:1 to about 15:1. Preferably the extraction is conducted at a temperature of from about −20° C. to about 100° C., more preferably from about −10° C. to about 80° C., and most preferably from about 0° C. to about 60° C. The extraction is usually conducted at normal atmospheric pressure, however, higher or lower pressure conditions may be used by those skilled in the art. Pressure is preferably about 100 psig or less; more preferably about 50 psig or less, and most preferably about 20 psig or less.

The sulfuric acid/HF mixture from the sulfuric acid absorber is fed to a HF recovery column. The HF and sulfuric acid may then be recycled. That is, the HF may be recirculated to the step (a) starting reaction for the formation of the hydrofluorocarbon, such as HFC-32, HFC-143a, HFC-245fa, HFC-236fa, or HFC-365mfc, and the sulfuric acid may be recycled for use in the extraction step. The organic portion of the mixture exiting the sulfuric acid absorber is optionally fed into a distillation column.

The distillation column is used to remove heavy reaction products. The pressure of this column is preferably maintained at from about 200 psig or less, more preferably from about 150 psig or less and most preferably from about 100 psig or less. The overhead of the distillation column contains hydrofluorocarbon, volatile by-products as impurities and some unreacted HF. The bottom cuts of the distillation column contains recyclable and non-recyclable heavies. The recyclable heavies are recycled back to the step (a) reactor. The non-recyclable heavies are disposed of.

Alternatively the sulfuric acid absorber may be replaced by a HF/water azeotrope absorber. The HF/water azeotrope weight ratio is preferably maintained at about 30% HF and 70% water. HF is extracted and recycled back to the reactor in the same manner as in the sulfuric acid.

The hydrofluorocarbon-rich stream exiting either the distillation column or the sulfuric acid absorber is fed to a caustic or water scrubber for removal of acidity. Such a scrubber is well known in the art and conventionally comprises a caustic scrubbing with aqueous NaOH or KOH under conditions sufficient to neutralize residual acidity.

A photochlorination unit is then used to remove unsaturates in the hydrofluorocarbon, e.g. HFC-32, HFC-143a, HFC-245fa, HFC-236fa, or HFC-365mfc, stream. This is done by adding chlorine to the stream to react with unsaturates in the presence of UV light. Photochlorination of unsaturates is itself well known in the art. The mole ratio of $Cl_2$/total unsaturates is preferably about 5 or less, more preferably about 4 or less, and most preferably about 3 or less. Pressure is not critical, although it is preferably operated under atmospheric or subatmospheric pressure. Temperature is preferably about 60° C. or less, more preferably about 40° C. or less and most preferably about 25° C. or less. UV light preferably has a wavelength of less than about 400 nanometers. The mixture is exposed to the UV light for a time and at an energy level sufficient to reduce unsaturates to less than about 500 ppm. The acidity of the resulting stream was removed once again using water and/or caustic scrubbers.

Hydrofluorocarbons may then be recovered in a step by distillation of the resulting crude product stream. Distillation can be a batch or continuous distillation. In the batch mode, one distillation column is sufficient. In a continuous mode, two distillation columns may be required, one to remove light distillates and the other to remove heavies. Pressure of the distillation(s) is preferred to run at about 200 psig or less, more preferably about 150 psig or less and most preferably about 100 psig or less.

The hydrofluorocarbon, i.e. HFC-32, HFC-143a, HFC-245fa, HFC-236fa, HFC-365mfc, but not limited thereto, produced has a purity of at least about 99.5%. The reactions of the present invention may be conducted in either a batch or continuous mode of operation, however, continuous operation is preferred.

The following non-limiting examples serve to illustrate the invention.

EXAMPLE 1

About 400 lbs antimony pentachloride catalyst were charged into a 50 gallon reactor. About 80 lbs of anhydrous HF were added to the reactor. The reactor temperature was raised to about 95° C. HCl was vented out of the reactor. About 300 lbs/day of methylene chloride ($CH_2Cl_2$), 141 lbs/day of fresh HF, 917 lbs/day of recycled/recovered HF and 20 lbs/day of chlorine are fed to the reactor continuously. The HF to methylene chloride ratio is about 15/1. Chlorine was used to keep catalyst active. The reactor pressure is maintained at about 200 psig. About 174 lbs of HFC-32 (99.9% purity) are produced. About 9.5 lbs of by-products are also produced.

EXAMPLE 2 COMPARATIVE

About 400 lbs antimony pentachloride catalyst was charged into a 50 gallon reactor. About 80 lbs of anhydrous HF was added to the reactor. The reactor temperature was raised to about 95° C. HCl was vented out of the reactor. About 300 lbs/day of methylene chloride ($CH_2Cl_2$), 282 lbs/day of fresh HF, no recycled/recovered HF and 20 lbs/day of chlorine are fed to the reactor continuously. The HF to methylene chloride ratio is about 4/1. Chlorine is used to keep catalyst active. The reactor pressure is maintained at about 200 psig. About 156 lbs of HFC-32 (99.9% purity) is produced. About 28 lbs of by-products were also produced.

EXAMPLE 3

About 400 lbs antimony pentachloride catalyst were charged into a 50 gallon reactor. About 80 lbs of anhydrous HF were added to the reactor. The reactor temperature was raised to about 95° C. HCl was vented out of the reactor. About 400 lbs/day of 1,1,1-trichloroethane (HCC-140a), 180 lbs/day of fresh HF, 719 lbs/day of recycled/recovered HF and 20 lbs/day of chlorine are fed to the reactor continuously. The HF to HCC-140a ratio is about 15/1. Chlorine is used to keep catalyst active. The reactor pressure is maintained at about 150 psig. About 240 lbs of HFC-143a (99.9% purity) is produced. About 12 lbs of high boiling point by-products are also produced.

EXAMPLE 4 COMPARATIVE

About 400 lbs antimony pentachloride catalyst was charged into a 50 gallon reactor. About 80 lbs of anhydrous HF was added to the reactor. The reactor temperature was raised to about 95° C. HCl was vented out of the reactor. About 400 lbs/day of 1,1,1-trichloroethane (HCC-140a), 300 lbs/day of fresh HF, no recycled/recovered HF and 20 lbs/day of chlorine are fed to the reactor continuously. The HF to HCC-140a ratio was about 5/1. Chlorine was used to keep catalyst active. The reactor pressure is maintained at about 150 psig. About 214 lbs of HFC-143a (99.9% purity) are produced. About 38 lbs of high boiling point by-products are also produced.

EXAMPLE 5

About 400 lbs antimony pentachloride catalyst was charged into a 50 gallon reactor. About 80 lbs of anhydrous HF was added to the reactor. The reactor temperature was raised to about 95° C. HCl was vented out of the reactor. About 605 lbs/day of HCC-240fa, 280 lbs/day of fresh HF, 684 lbs/day of recycled/recovered HF and 20 lbs/day of chlorine were fed to the reactor continuously. The HF to HCC-240fa ratio was about 17/1. Chlorine was used to keep catalyst active. The reactor pressure was maintained at about 150 psig. About 340 lbs of HFC-245fa (99.9% purity) was produced. About 36.4 lbs of high boiling point by-products were also produced.

EXAMPLE 6

About 400 lbs antimony pentachloride catalyst was charged to a 50 gal reactor. About 80 lbs of anhydrous HF was added to the reactor. The reactor temperature was raised to about 95° C. HCl was vented out of the reactor. About 605 lbs/day HCC-240fa, 280 lbs/day of fresh HF, 1128 lbs/day of recycled/recovered HF and 20 lbs/day chlorine were fed to the reactor continuously. The HF to HCC-240fa ratio was about 25/1. Chlorine was used to keep catalyst active. The reactor pressure was maintained at about 150 psig. About 345 lbs of HFC-245fa (99.9% purity) was produced. About 21 lbs of high boiling point by-products were also produced.

EXAMPLE 7 COMPARATIVE

About 400 lbs antimony pentachloride catalyst was charged to a 50 gal reactor. About 80 lbs of anhydrous HF was added to the reactor. The reactor temperature is raised to about 95° C. HCl was vented out of the reactor. About 605 lbs/day HCC-240fa, 280 lbs/day of fresh HF, 461 lbs/day of recycled/recovered HF and 20 lbs/day chlorine were fed to the reactor continuously. The HF to HFC-240fa ratio was about 13/1. Chlorine was used to keep catalyst active. The reactor pressure was maintained at about 150 psig. About 320 lbs of HFC-245fa (99.9% purity) was produced. About 50 lbs of high boiling by-products were also produced.

As one can see, the processes of Examples 1, 3, 5 and 6 produce a substantially larger yield of HFC-32, HFC-143a, HFC-245fa and a much lower amount of high boiling point by-products While the present invention has been particularly shown and described with reference to preferred embodiments, it will be readily appreciated by those of ordinary skill in the art that various changes and modifications may be made without departing from the spirit and scope of the invention. It is intended that the claims be interpreted to cover the disclosed embodiment, those alternatives which have been discussed above and all equivalents thereto.

What is claimed is:

1. A continuous, integrated manufacturing process for the preparation of a hydrofluorocarbon which comprises
   (a) reacting at least one hydrochlorocarbon with hydrogen fluoride in the presence of a fluorination catalyst, wherein the hydrogen fluoride to hydrochlorocarbon mole ratio is at least about 15:1;
   (b) optionally recycling a portion of any unreacted HF back to step (a);
   (c) continuously adding sufficient chlorine to keep the activity of the fluorination catalyst;
   (d) removing any HCl produced by step (a); and
   (e) recovering at least one hydrofluorocarbon.

2. The process of claim 1 wherein the recycling of step (b) is conducted.

3. The process of claim 1 wherein step (d) is conducted by distillation.

4. The process of claim 1 wherein step (a) is conducted in a liquid phase.

5. The process of claim 1 wherein the hydrochlorocarbon comprises methylene chloride; 1,1,1-trichloroethane; 1,1,1,3,3-pentachloropropane; 1,1,1,3,3,3-hexachloropropane; 1,1,1,3,3-pentachlorobutane; 1,1,1,3,3-pentachloropropane; perchloroethylene or combinations thereof.

6. The process of claim 1 wherein the hydrochlorocarbon comprises 1,1,1,3,3-pentachloropropane and wherein the hydrofluorocarbon comprises 1,1,1,3,3-pentafluoropropane.

7. The process of claim 1 wherein the fluorination catalyst is selected from the group consisting of transition metal halides and oxides, Group IVb metal halides, Group Vb metal halides and combinations thereof.

8. The process of claim 1 wherein the fluorination catalyst is selected from the group consisting of fluorinated chrome halides, fluorinated chrome oxides, fluorinated species of $SbCl_5$, $SbCl_3$, $TaCl_5$, $SnCl_4$, $NbCl_5$, $TiCl_4$, $MoCl_5$ and combinations thereof.

9. The process of claim 1 wherein the hydrogen fluoride to hydrochlorocarbon mole ratio ranges from about 15:1 to about 50:1.

10. The process of claim 1 wherein the hydrogen fluoride to hydrochlorocarbon mole ratio ranges from about 15:1 to about 40:1.

11. The process of claim 1 wherein the hydrogen fluoride to hydrochlorocarbon mole ratio ranges from about 15:1 to about 30:1.

12. The process of claim 1 wherein step (a) is conducted at a temperature of from about 60° C. to about 180° C.

13. The process of claim 1 wherein step (a) is conducted at a pressure of from about 20 to about 400 psig.

14. The process of claim 1 which comprises recovering any hydrogen fluoride present after step (b).

15. The process of claim 1 which comprises recovering any hydrogen fluoride present after step (b) and then recycling the recovered hydrogen fluoride to step (a).

16. The process of claim 1 further comprising the subsequent step (e) of removing any unsaturated compounds present after step (e) by photochlorination.

17. The process of claim 1 wherein step (e) comprises recovering hydrofluorocarbon from the result of step (d) by distillation.

18. The process of claim 1 further comprising an additional step after step (d) and before step (e), comprising distilling the product resulting from step (d) to produce an overhead of the distillation column comprising a hydrofluorocarbon, hydrogen fluoride, unsaturated compounds and other impurities.

19. The process of claim 18 wherein the additional distilling step after step (d) and before step (e) is conducted at a pressure of about 200 psig or less.

20. The process of claim 1 wherein step (e) is conducted by liquid-vapor extraction.

21. The process of claim 1 wherein step (e) is conducted by extracting the HF/hydrofluorocarbon stream with sulfuric acid to the product resulting after step (d) and then separating therefrom a mixture of sulfuric acid and HF from a reaction mass balance comprising hydrofluorocarbon, unsaturated compounds and other impurities.

22. The process of claim 21 comprising the step of removing residual acids from said reaction mass balance after step (e).

23. The process of claim 22 wherein the step of removing residual acids from said reaction mass balance after step (e) is conducted with a caustic scrubber or a water scrubber.

24. The process of claim 21 further comprising separating sulfuric acid and HF from the mixture of sulfuric acid and HF.

25. A continuous, integrated manufacturing process for the preparation of a hydrofluorocarbon which comprises (a) reacting at least one hydrochlorocarbon with hydrogen fluoride, in the presence of a fluorination catalyst, and wherein the hydrogen fluoride to hydrochlorocarbon mole ratio is at least about 15:1;
(b) optionally recycling a portion of any unreacted HF back to step (a);
(c) continuously adding sufficient chlorine to keep the activity of the fluorination catalyst;
(d) removing any HCl produced by step (a);
(e) optionally recovering any additional unreacted HF present after step (d) by liquid-vapor or liquid-liquid extraction;
(f) optionally removing unsaturated compounds present after step (e) by photochlorination; and
(g) recovering at least one hydrofluorocarbon from the result of step (f) by distillation.

26. The process of claim 25 wherein the recycling of step (b) is conducted.

27. The process of claim 25 wherein step (d) is conducted by distillation.

28. The process of claim 25 wherein step (a) is conducted in a liquid phase.

29. The process of claim 25 wherein the hydrochlorocarbon comprises methylene chloride; 1,1,1-trichloroethane; 1,1,1,3,3-pentachloropropane; 1,1,1,3,3,3-hexachloropropane; 1,1,1,3,3-pentachlorobutane and combinations thereof.

30. The process of claim 25 wherein the hydrochlorocarbon comprises 1,1,1,3,3-pentachloropropane and wherein the hydrofluorocarbon comprises 1,1,1,3,3-pentafluoropropane.

* * * * *